United States Patent [19]

Weissman et al.

[11] Patent Number: 5,511,693
[45] Date of Patent: Apr. 30, 1996

[54] ORAL IRRIGATION APPARATUS AND METHOD OPERABLE FROM A PRESSURIZED WATER SUPPLY FOR SELECTIVELY DISCHARGING A PLURALITY OF LIQUIDS

[75] Inventors: William R. Weissman, North Hollywood; Peter Liapis, Los Angeles; George Sanchez; Bernardo Baran, both of Woodland Hills, all of Calif.

[73] Assignee: William R. Weissman, North Hollywood, Calif.

[21] Appl. No.: 255,928

[22] Filed: Jun. 7, 1994

[51] Int. Cl.⁶ .................................................... B67D 5/56
[52] U.S. Cl. ........................... 222/1; 222/144.5; 222/389
[58] Field of Search ........................ 222/1, 144.5, 387, 222/389, 335

[56] References Cited

U.S. PATENT DOCUMENTS

| | | | |
|---|---|---|---|
| 923,550 | 6/1909 | Mikorey | 222/389 |
| 2,708,600 | 5/1955 | Froidevaux | 222/389 X |
| 2,867,230 | 1/1959 | Bletcher et al. | 137/119 |
| 3,225,759 | 12/1965 | Drapen et al. | |
| 4,043,337 | 8/1977 | Baugher | 128/229 |
| 4,265,229 | 5/1981 | Rice | 128/66 |
| 4,564,005 | 1/1986 | Merchand | 128/66 |
| 4,793,331 | 12/1988 | Stewart | 128/66 |
| 4,875,626 | 10/1989 | Buhler et al. | 222/144.5 X |
| 5,004,158 | 4/1991 | Halem et al. | |

FOREIGN PATENT DOCUMENTS

| | | | |
|---|---|---|---|
| 0327757 | 8/1989 | European Pat. Off. | 222/389 |
| 308960 | 9/1917 | Germany | 222/389 |

*Primary Examiner*—Andres Kashnikow
*Assistant Examiner*—Kenneth Bomberg
*Attorney, Agent, or Firm*—Ashen, Golant & Lippman

[57] ABSTRACT

An oral irrigating liquid dispenser (20) is disclosed which operates from a liquid pressure source (22) to dispense two liquids (54, 72) from an orifice (26). A valve member (24) moves to different positions to couple the source respectively to a piston face (64A), a conduit (60) and an outlet port (71). Flow control valves (80, 89) are provided to control flow from the orifice. Since no electrical power is involved the dispenser may safely be used in the presence of liquids and electrical grounds.

18 Claims, 4 Drawing Sheets

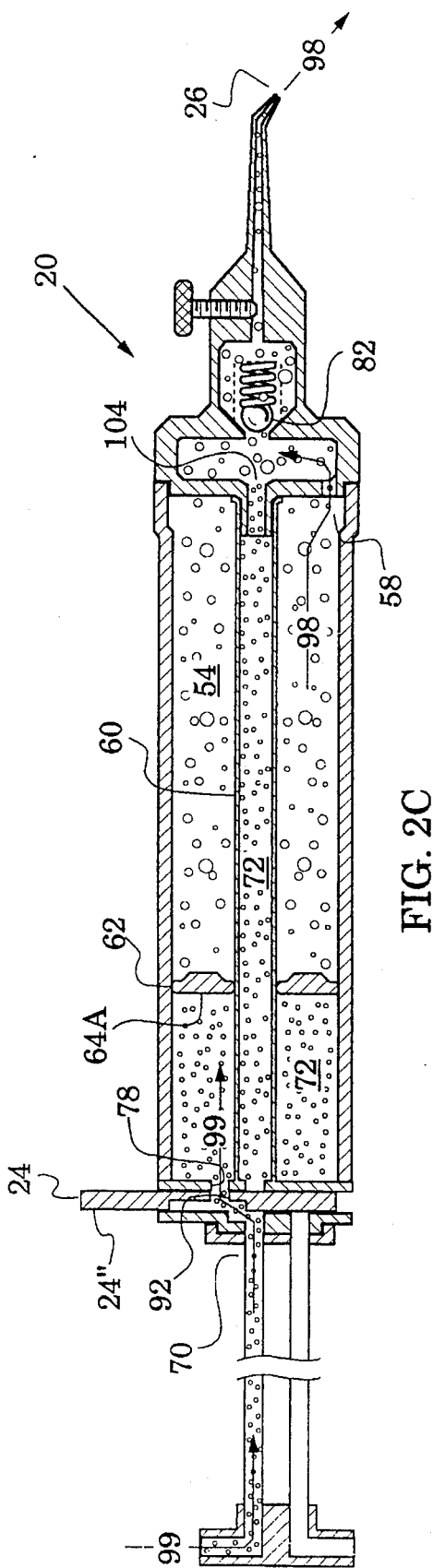
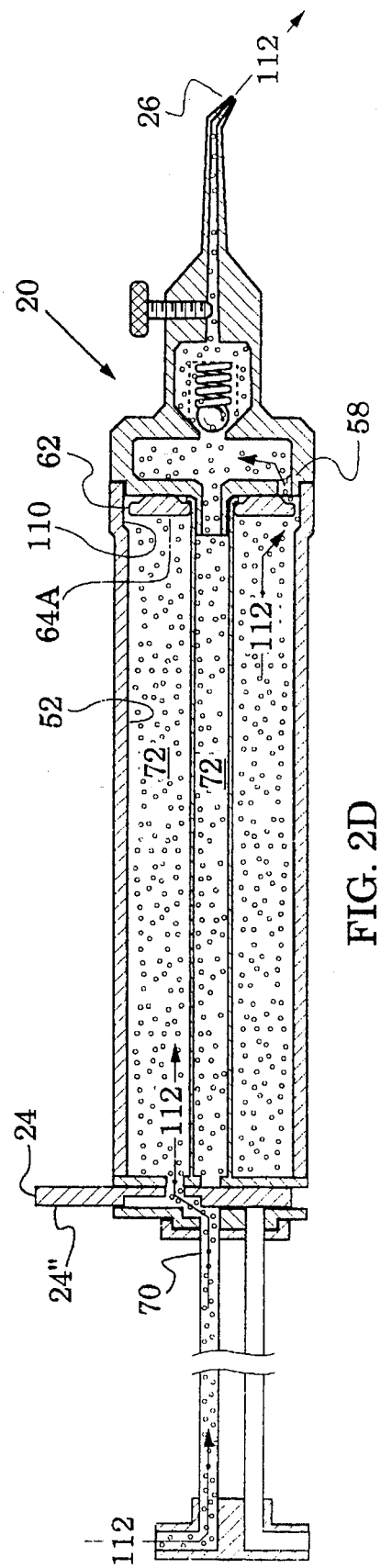

1

ORAL IRRIGATION APPARATUS AND METHOD OPERABLE FROM A PRESSURIZED WATER SUPPLY FOR SELECTIVELY DISCHARGING A PLURALITY OF LIQUIDS

TECHNICAL FIELD

The present invention relates generally to a liquid dispensing apparatus for dental purposes and more particularly to such apparatus for mixing and applying a cleansing stream to teeth and/or gums.

BACKGROUND ART

Dental oral irrigating apparatus presently exists for generating and applying a stream of liquid to areas of a person's mouth. Some such apparatus are electrically powered and present potential danger to the user.

Other such apparatus are powered and controlled by the liquid pressure from a water line. In particular prior U.S. Pat. Nos. to Drapen, 3,225,759 and to Halem, et al., 5,004,158 (embodiment of FIG. 2) disclose dental oral irrigating apparatus powered and controlled by water line pressure and having movable pistons for discharging a secondary or supplemental liquid. These prior art devices do not however disclose a selectively operable valve to selectively couple an inlet port from the water supply to either (1) the outlet orifice of the irrigating apparatus or (2) the face of the piston opposed to the secondary liquid.

DISCLOSURE OF INVENTION

The present invention is directed to oral irrigating apparatus for liquid dispensing.

Apparatus in accordance with the invention are characterized by an inlet port for receiving a liquid 1 from a pressurized supply, a chamber for holding a liquid 2, a piston disposed therein, a conduit, an orifice communicating with the chamber and conduit and a valve for selectively coupling the inlet port to either the conduit or the piston thereby respectively dispensing liquid 1 or liquid 2 from the orifice.

In a preferred embodiment the valve may also selectably couple the inlet port to an outlet port to direct the liquid 1 away from the apparatus.

In a preferred embodiment the apparatus is directed especially to irrigation of teeth and gums with a liquid 1 (water) and a liquid 2 (mouthwash).

In accordance with a feature of the invention, no electrical power is used so that embodiments of the invention may be safely used.

MODES FOR CARRYING OUT THE INVENTION

Figure 1:
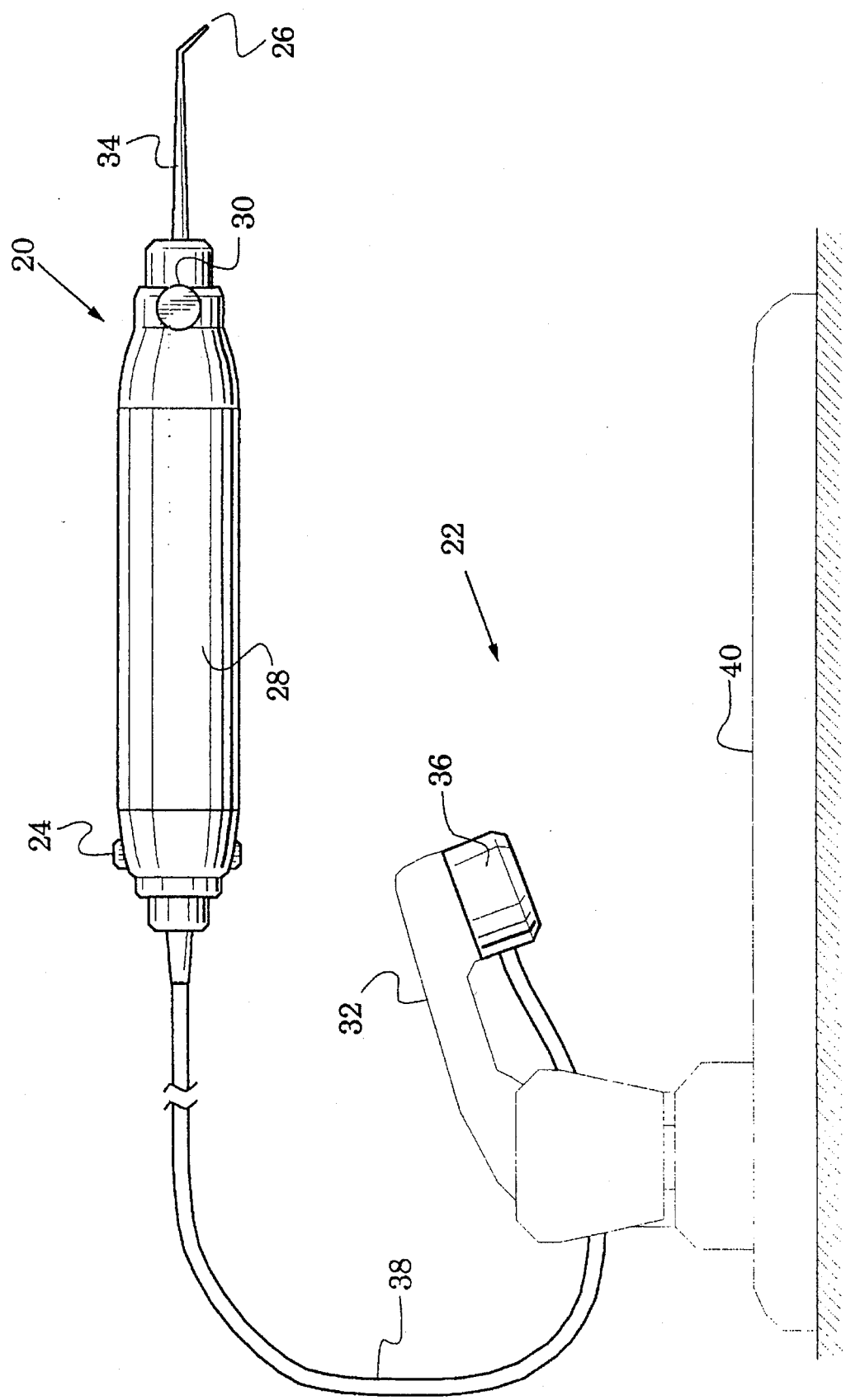
FIG. 1 illustrates a preferred apparatus embodiment, in accordance with the present invention, coupled to a pressurized liquid 1 supply.

FIG. 1 is an elevation view of a preferred embodiment 20, in accordance with the present invention, of a portable oral irrigating apparatus coupled to a pressurized supply 22 of a liquid 1 such as water. In response to movement of a mode selector member 24 to first and second "On" positions from a third or "Off" position, the embodiment 20 respectively dispenses a liquid 1 and a liquid 2 from its orifice 26. The liquid 1 is that received from the supply 22 while the liquid 2 is any liquid placed in a chamber defined within the housing 28. The flow rate of either liquid from the orifice 26 is adjusted via a knob 30 of a flow rate control valve.

Embodiments of the invention generally may be directed to the dispensing of various liquids. The embodiment 20 is particularly directed to dispensing water (liquid 1) or mouthwash (liquid 2) and is configured to operate from a pressurized supply of liquid I illustrated in the form of a countertop sink tap 32. Accordingly, the orifice 26 is configured in the form of a dental syringe 34 to facilitate irrigation of teeth and gums. In other embodiments of the invention the orifice may assume other configurations to facilitate application of particular liquids 1 and 2.

The embodiment 20 is coupled to the tap 32 via a diverter 36 and bidirectional hose 38 which sends liquid 1 to the housing 28. In the "Off" position of the mode selector member 24, the liquid 1 is directed back through the hose 38 to issue from the diverter 36 into the sink 40.

In accordance with features of the invention, the embodiment 20 is portable, easily operated with one hand and requires only a pressurized liquid supply for operation. Thus, for example, it can be carried in luggage and quickly connected to a supply such as the sink tap 32. Since no electrical power is associated with its operation, it may be safely used in the presence of water and electrical grounds.

Figure 2A:
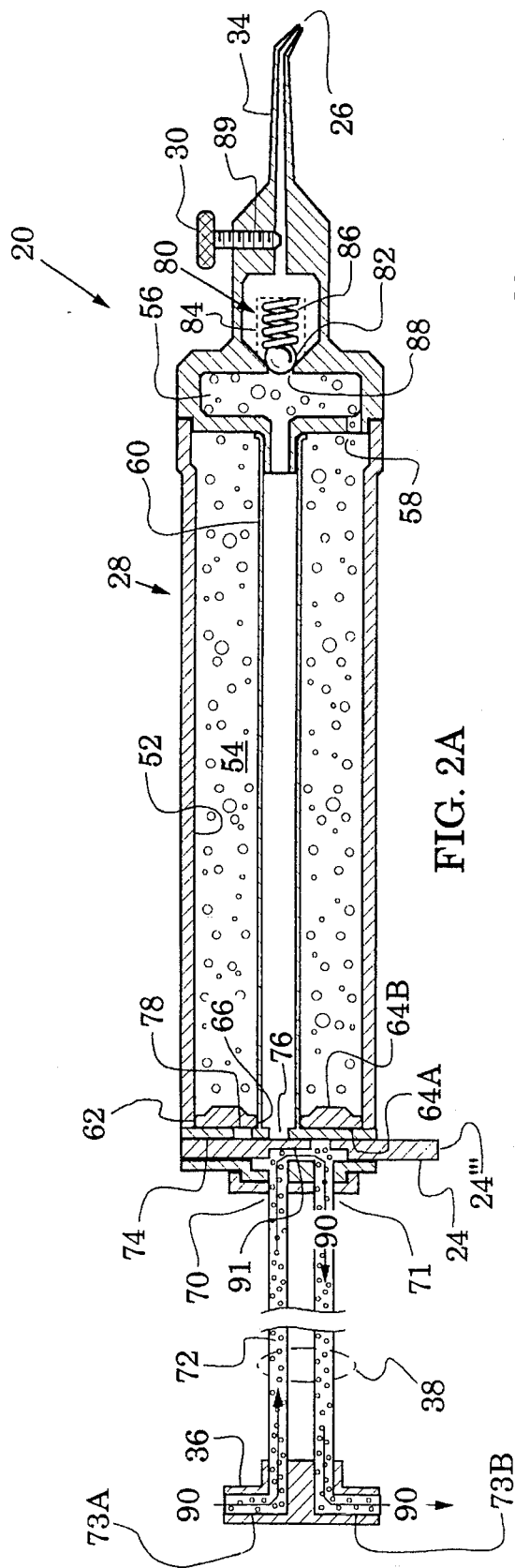
FIG. 2 is a sectional view of the embodiment of FIG. 1 illustrating an operational mode thereof.
FIG. 2B is a sectional view of the embodiment of FIG. 1 illustrating another operational mode thereof.
FIG. 2C is a sectional view of the embodiment of FIG. 1 illustrating another operational mode thereof.
FIG. 2D is a sectional view of the embodiment of FIG. 1 illustrating another operational mode thereof.

Attention is now directed to structural details of the embodiment 20 as illustrated in the sectional views of FIGS. 2A–2D. Each of these figures show an operational mode of the embodiment. In FIG. 2A, the mode control member 24 is in the above described "Off" position, n while in FIGS. 2B, 2C it is respectively in the first and second positions. FIG. 2D shows a fourth operational mode in which the member 24 remains in the second position.

It will be understood that the nomenclature of these member positions is arbitrary and for descriptive purposes only. The sequence of the figures generally tracks the amount of liquid 2 in the chamber 52, i.e. in FIGS. 2A, 2B the chamber is filled with liquid 2, in FIG. 2C is is partly filled with liquid 2 and in FIG. 2D it contains only liquid 1.

In FIG. 2A the housing 28 defines a chamber 52 to hold the liquid 2 (reference number 54) and communicate with the orifice 26 via a subchamber 56 and vent 58. The housing also defines a conduit 60 which communicates with the orifice 26 through the subchamber 56.

A piston 62 having first and second faces 64A, 64B is slidably received in the chamber 52. The piston 62 defines an opening 66 which slidably receives the conduit 60. Inlet port 70 and outlet port 71 are defined by the housing 28 to respectively receive the liquid I (reference number 72) from the pressurized supply via the diverter 36 and return it to the diverter (for clarity of illustration, liquid 1 distinguished from liquid 2 by having smaller air bubbles trapped therein). This exchange is conducted via first and second passages 73A, 73B defined by the diverter 36 and bidirectional hose 38 connected therefrom to ports 70, 71.

The housing 28 also defines a channel 74 to communicate with the conduit 60, the piston first face 64A, the inlet port 70 and outlet port 71. The channel 74 includes apertures 76, 78 to facilitate this communication. The mode selector member 24 shown in FIG. 1 is seen, to be a valve member which is slidably received in the channel 74.

A flow control a check valve 80, responsive to pressure from the liquid 1 supply (22 in FIG. 1), is designed to block the flow of all liquids through the orifice 26 in the absence of such pressure. In the configuration 20, this valve is formed by a ball 82 within a permeable cage 84. The ball 82 is urged by a spring 86 into a seat 88. A flow control valve responsive to adjustment by a user of the apparatus is formed by the screw 89 threadedly mounted in the housing 28 to restrict the flow through the orifice 26. The screw 89 terminates in the knob 30.

Although the housing 28 has been structurally described above as an integral piece it should be understood that it may be comprised of various mated parts. FIG. 2A shows one possible arrangement of such parts.

Attention is now directed to operational modes of the embodiment 20. As mentioned above, FIG. 2A shows the valve member 24 in its "Off" position 24'" wherein the liquid 1 is directed back to the diverter 36 as indicated by arrows 90. The liquid flow is enabled by a passage 91 defined by the valve member 24. The How control valve ball 88 is seated thereby preventing leakage of liquid 2 from the orifice 26. In FIG. 2A it is assumed that chamber 52 has been filled with liquid 2 so that the piston 62 is proximate to the valve member 24 with its second face 64B abutting the liquid 2. Although the figure shows the conduit 60 to be empty, some liquid 2 may be present depending on the method of filling and the amount of air trapped in the conduit.

Figure 2B:
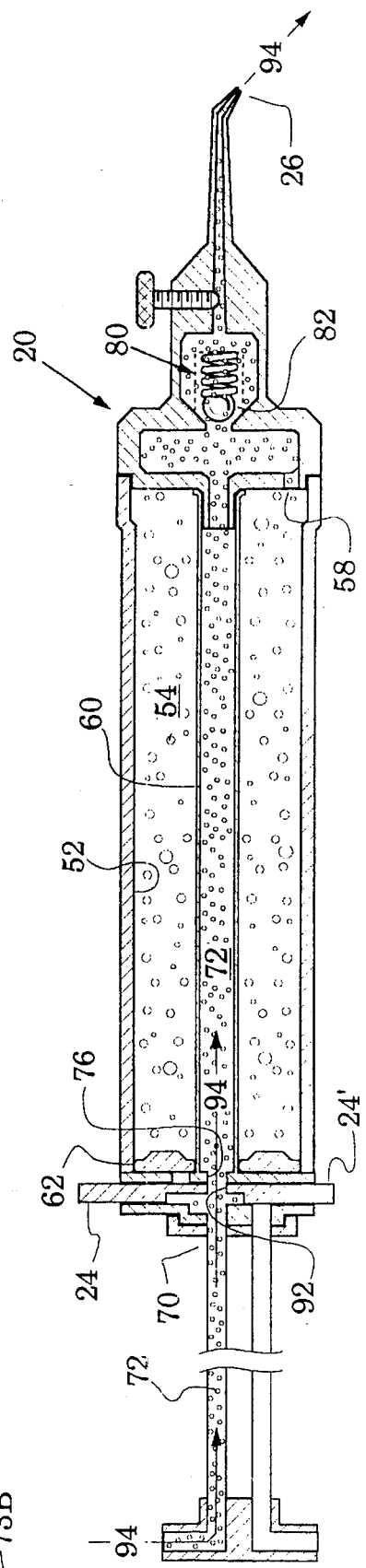

In FIG. 2B, the valve member 24 has been moved to the first position 24' where a passage 92 of the valve member aligns with aperture 76 to couple the inlet port 70 with the conduit 60. The pressure thus coupled to the flow control or check valve 80 forces the ball 82 from its seat 88 and the liquid 1 flows through the conduit 60 and is discharged through the orifice 26 as indicated by arrows 94. The piston 62 and liquid 2 remain in place within the chamber 52 as pressure between the liquids is automatically equalized across the vent 58 except for diffusion and eddy mixing.

In FIG. 2C, the valve member 24 has been moved to the second position 24" where the valve member passage 92 aligns with aperture 78 to couple the inlet port 70 with the piston first face 64A. Consequently, in response to urging of the piston 62, liquid 2 forces the ball 82 from its seat and flows through the vent 58 to be discharged through orifice 26 as indicated by arrows 98. Liquid 1 flows to replace liquid 2 behind the piston first face 64A as indicated by arrows 99. Since the conduit 60 is now closed at one end, liquid 1 therein remains in place with pressure between the liquids automatically equalized across their interface 104.

In FIG. 2D, valve member 24 remains in the second position 24". All of liquid 2 has been forced from the chamber 52 and discharged through orifice 26. Piston 62 has been forced to enter an enlarged portion 110 of the chamber 54. The enlarged portion 110 couples (provides passage between) the orifice 26 and the piston first face 64A. Consequently, liquid 1 flows around the piston 62 and through vent 58 to be discharged through the orifice 26 as indicated by arrows 112. It should be understood that other preferred embodiments may realize the coupling between the orifice and the piston first face in other ways, e.g., a channel cut into the chamber 52 wall.

Thus, as shown in FIGS. 2A–2D, a user of the embodiment 20 may move the mode control member 24 to command either liquid 1 or 2 to be discharged through the orifice 26 as desired when liquid 2 is commanded and the supply of liquid 2 within chamber 52 is exhausted, liquid 1 will then automatically issue from the orifice. When the member 24 is placed in the "OFF" position shown in FIG. 2A, liquid 1 flows back to the diverter 36 and into the sink 40 as shown in FIG. 1, and no liquids are discharged through orifice 26.

Figure 3A:
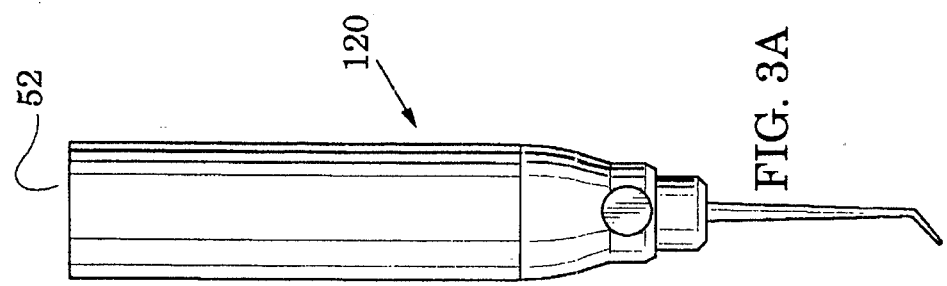
FIG. 3A is a side view of a disassembled portion of the apparatus of FIG. 1.
Figure 3B:
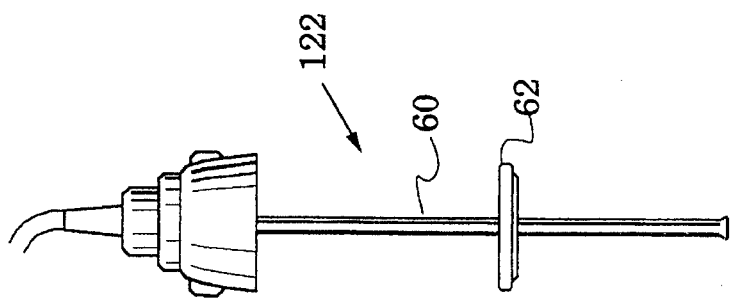
FIG. 3B is a side view of another disassembled portion of the apparatus of FIG. 1.

FIGS. 3A, 3B are side views illustrating disassembled portions 120, 122 of the embodiment 20 of FIG. 1. The portion 122 includes the conduit 60 and piston 62 as shown, for example, in FIG. 2A while portion 120 includes the chamber 52. The chamber 52 is thus exposed for refilling with liquid 2. In this embodiment, the conduit 60 is flared at one end to retain the piston 62.

Figure 3C:
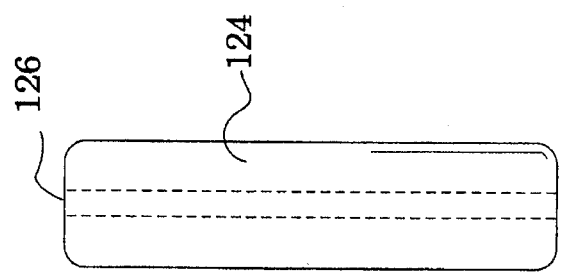
FIG. 3C is a side view of a puncturable cartridge for use with the apparatus of FIG. 1.

Liquid 2 may be poured into the chamber 52. Alternatively, FIG. 3C shows a frangible cartridge 124 which may be filled with liquid 2 and conveniently inserted into the chamber 52. A bore 126 is defined by the cartridge 124 to receive the conduit 60. Once the portions 120, 122 are reassembled, the cartridge may be ruptured by pressure thereon. This rupture may be facilitated by the presence of a sharp extension defined inward from the walls of the chamber 52.

The diverter 36 may be formed to mate with the tap 32 (shown in FIG. 1) in ways well known in the art (e.g. threaded to match the tap threads, equipped with a quick disconnect sleeve).

From the foregoing it should now be recognized that a liquid dispenser has been disclosed herein configured to operate with pressure from a liquid 1 source. Embodiments in accordance with the invention may be configured for special applications such as irrigation of the teeth and gums. Because they do not use electrical power, apparatus in accordance with the present invention may safely be used in the presence of fluids and electrical grounds.

The preferred embodiments of the invention described herein are exemplary and numerous modifications, dimensional variations and rearrangements can be readily envisioned to achieve an equivalent result, all of which are intended to be embraced within the scope of the appended claims.

What is claimed is:

1. Liquid dispensing dental apparatus operative from a pressurized supply of a liquid 1, comprising:

a housing defining a chamber for holding a liquid 2, said housing further defining an orifice communicating with said chamber and an inlet port for receiving said liquid 1 from said pressurized supply;

a piston having first and second faces, said piston slidably received in said chamber with said second face abutting said liquid 2;

a conduit defined by said housing to communicate with said orifice; and valve means for coupling said inlet port with a selectable one of said conduit and said piston first face.

2. The apparatus of claim 1 wherein said housing further defines an outlet port and said valve means comprises means for selectively directing liquid 1 from said inlet port to said outlet port.

3. The apparatus of claim 1 wherein said chamber includes an endwall; and further comprising:

means, responsive to said piston positioned proximate to said endwall, for coupling said orifice with said piston first face.

4. The apparatus of claim 2 wherein said valve means comprises:

a channel defined by said housing to communicate with said piston first face, said inlet port and said outlet port; and a valve member slidably received in said channel.

5. The apparatus of claim 3 wherein said orifice coupling means comprises an enlarged chamber portion defined by said housing proximate to said endwall.

6. The apparatus of claim 1 further comprising valve means for selectively restricting said orifice.

7. The apparatus of claim 1 further comprising valve means, responsive to pressure from said supply, for blocking said orifice.

8. The apparatus of claim 2 further comprising:

a diverter defining a first and second passages; and means for coupling said diverter first and second passages respectively to said inlet port and said outlet port.

9. Liquid dispensing dental apparatus operative from a pressurized supply of a liquid 1, comprising:

a housing defining a chamber for holding a liquid 2, said housing further defining an orifice communicating with said chamber and an inlet port for receiving said liquid 1 from said pressurized supply;

a piston having first and second faces, said piston slidably received in said chamber with said second face abutting said liquid 2;

a conduit defined by said housing to communicate with said orifice;

a channel defined by said housing to communicate with said inlet port, said piston first face and said, conduit; and a valve member slidably received in said channel for movement between first and second position, said valve member defining a first passage to couple, in said first position, said inlet port with said conduit, and to couple, in said second position, said inlet port with said piston first face.

10. The apparatus of claim 9 wherein:

said housing defines an outlet port to communicate with said channel;

said valve member moves within said channel to a third position; and said valve member defines a second passage to couple, in said third position, said inlet port and said outlet port.

11. The apparatus of claim 9 wherein said chamber has an enlarged portion to couple said orifice with said piston first face when said piston is within said portion.

12. The apparatus of claim 9 wherein said piston defines an opening to slidably receive said conduit therein.

13. The apparatus of claim 10 further comprising a first flow control valve, responsive to pressure from said supply, arranged to block said orifice when said valve member is in said third position.

14. The apparatus of claim 9 further comprising a second flow control valve, responsive to adjustment by a user of said apparatus, arranged to restrict said orifice.

15. The apparatus of claim 10 further comprising:

a diverter defining a first and second passages; and means for coupling said diverter first and second passages respectively to said inlet port and said outlet port.

16. A method for dental purposes of dispensing liquids in response to a pressurized supply of a liquid 1, comprising the steps of:

providing a housing;

defining, with said housing, a chamber for holding a liquid 2, an orifice communicating with said chamber and an inlet port for receiving said liquid 1 from said pressurized supply;

providing a piston having first and second faces;

receiving said piston slidably in said chamber with said second face abutting said liquid 2;

defining, with said housing, a conduit to communicate with said orifice; and coupling said inlet port with a selectable one of said conduit and said piston first face to respectively dispense said liquid 1 or said liquid 2 from said orifice.

17. The method of claim 16 further comprising the steps of:

defining, with said housing, an outlet port; and coupling said inlet port and said outlet port to direct said liquid 1 therebetween.

18. The method of claim 16 further comprising the steps of:

defining, with said housing, an endwall of said chamber; and coupling, when said piston is proximate to said endwall, said orifice with said piston first face to dispense said liquid 1 from said orifice.

* * * * *

UNITED STATES PATENT AND TRADEMARK OFFICE
CERTIFICATE OF CORRECTION

PATENT NO. : 5,511,693
DATED : April 30, 1996
INVENTOR(S) : William R. Weissman et al.

It is certified that error appears in the above-indentified patent and that said Letters Patent is hereby corrected as shown below:

Col. 1, line 59, change "Fig. 2" to --Fig. 2A--.

Col. 2, line 49, after "position" delete --n--.

Col. 3, line 4, before "distinguish" add --is--.

Col. 3, line 13, after "seen" delete --,--.

Col. 3, line 15, after "control" change "a" to --or--.

Col. 3, line 34, change "How" to --flow--.

Col. 4, line 12, change "desired when" to --desired. When--.

Col. 5, line 42, delete "," before "conduit ".

Col. 5, line 45, change "position" to --positions--.

Signed and Sealed this

Eighteenth Day of March, 1997

Attest:

BRUCE LEHMAN

Attesting Officer    Commissioner of Patents and Trademarks